(12) United States Patent
Pantages et al.

(10) Patent No.: US 8,313,498 B2
(45) Date of Patent: Nov. 20, 2012

(54) VASCULAR SUTURING DEVICE

(75) Inventors: Anthony J. Pantages, San Jose, CA (US); Brian A. Ellingwood, Sunnyvale, CA (US); Erik K. Walberg, Redwood City, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/022,050

(22) Filed: Feb. 7, 2011

(65) Prior Publication Data
US 2011/0196387 A1    Aug. 11, 2011

Related U.S. Application Data

(62) Division of application No. 11/199,515, filed on Aug. 8, 2005, now Pat. No. 7,883,517.

(51) Int. Cl.
*A61B 17/04* (2006.01)
(52) U.S. Cl. .................................................. 606/148
(58) Field of Classification Search .............. 606/139, 606/144, 145, 146, 147, 148, 151
See application file for complete search history.

(56) References Cited

U.S. PATENT DOCUMENTS

| | | | |
|---|---|---|---|
| 312,408 A | 2/1885 | Wackerhagen | |
| 597,165 A | 1/1898 | Hall | |
| 659,422 A | 10/1900 | Shidler | |
| 989,231 A | 4/1911 | Davis | |
| 1,574,362 A | 9/1922 | Callahan | |
| 1,625,602 A | 4/1927 | Gould et al. | |
| 1,940,351 A | 3/1933 | Howard | |
| 2,012,776 A | 8/1935 | Roeder | |
| 2,131,321 A | 10/1937 | Hart | |
| 2,127,903 A | 8/1938 | Bowen | |
| 2,371,978 A | 3/1945 | Perham | |
| 2,397,823 A | 4/1946 | Walter | |
| RE22,857 E | 3/1947 | Ogburn | |
| 2,595,086 A | 11/1948 | Larzelere | |
| 2,588,589 A | 3/1952 | Tauber | |
| 2,646,045 A | 7/1953 | Priestley | |
| 2,692,599 A | 10/1954 | Creelman | |
| 2,941,489 A | 6/1960 | Fischbein | |
| 2,959,172 A | 11/1960 | Held | |
| 3,033,156 A | 5/1962 | Verlish | |

(Continued)

FOREIGN PATENT DOCUMENTS

DE           912619         5/1954

(Continued)

OTHER PUBLICATIONS

U.S. Appl. No. 12/966,961, filed Dec. 13, 2010, Modesitt, et al.

(Continued)

*Primary Examiner* — Darwin Erezo
*Assistant Examiner* — Christina Lauer
(74) *Attorney, Agent, or Firm* — Workman Nydegger; Randy Shen

(57) ABSTRACT

A surgical device for suturing vascular vessels is described, as well as methods for suturing tissue employing the surgical device. The device includes a distal member for insertion into a vascular vessel puncture wound. The distal member contains a suture and needle engaging fitting. At least one needle is advanced through tissue adjacent the puncture wound and into the needle engaging fitting to draw lengths of suture material which can then be used to close the puncture wound.

15 Claims, 14 Drawing Sheets

U.S. PATENT DOCUMENTS

| | | |
|---|---|---|
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,587,115 A | 6/1974 | Shiley |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleischhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Ovil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liu et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bagnato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,312 A | 10/1994 | Brinkerhoff et al. |

| Patent | Date | Inventor |
|---|---|---|
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Della Badia et al. |
| 5,397,326 A | 3/1995 | Mangum |
| 5,403,329 A | 4/1995 | Hinchcliffe |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A * | 7/1995 | Sauer et al. ............ 606/139 |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,649,959 A | 7/1997 | Hannam et al. |
| 5,662,664 A | 9/1997 | Gordon et al. |
| 5,669,917 A | 9/1997 | Sauer et al. |
| 5,676,689 A | 10/1997 | Kensey et al. |
| 5,700,273 A | 12/1997 | Buelna et al. |
| 5,707,379 A | 1/1998 | Fleenor et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,814,069 A | 9/1998 | Schulze et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,897,487 A | 4/1999 | Ouchi |
| 5,897,564 A | 4/1999 | Schulze et al. |
| 5,902,311 A | 5/1999 | Andreas et al. |

| | | | | | | |
|---|---|---|---|---|---|---|
| 5,904,597 | A | 5/1999 | Doi et al. | 6,896,692 B2 | 5/2005 | Ginn et al. |
| 5,904,690 | A | 5/1999 | Middleman et al. | 6,911,034 B2 | 6/2005 | Nobles et al. |
| 5,904,697 | A | 5/1999 | Gifford, III et al. | 6,939,357 B2 | 9/2005 | Navarro et al. |
| 5,906,631 | A | 5/1999 | Imran | 6,964,668 B2 | 11/2005 | Modesitt et al. |
| 5,919,207 | A | 7/1999 | Taheri | 6,969,397 B2 | 11/2005 | Ginn |
| 5,921,994 | A | 7/1999 | Andreas et al. | 7,001,400 B1 | 2/2006 | Modesitt et al. |
| 5,928,266 | A | 7/1999 | Kontos | 7,029,480 B1 | 4/2006 | Klein et al. |
| 5,951,590 | A | 9/1999 | Goldfarb | 7,029,481 B1 | 4/2006 | Burdulis, Jr. et al. |
| 5,954,732 | A | 9/1999 | Hart et al. | 7,048,747 B2 | 5/2006 | Arcia et al. |
| 5,957,936 | A | 9/1999 | Yoon et al. | 7,063,710 B2 | 6/2006 | Takamoto et al. |
| 5,957,937 | A | 9/1999 | Yoon | 7,083,635 B2 | 8/2006 | Ginn |
| 5,957,938 | A | 9/1999 | Zhu et al. | 7,108,710 B2 | 9/2006 | Anderson |
| 5,964,773 | A | 10/1999 | Greenstein | 7,112,225 B2 | 9/2006 | Ginn |
| 5,964,782 | A | 10/1999 | Lafontaine et al. | 7,160,309 B2 | 1/2007 | Voss |
| 5,972,030 | A | 10/1999 | Garrison et al. | 7,179,266 B2 | 2/2007 | Kontos |
| 5,976,161 | A | 11/1999 | Kirsch et al. | 7,229,458 B2 | 6/2007 | Boecker et al. |
| 5,980,539 | A | 11/1999 | Kontos | 7,235,087 B2 | 6/2007 | Modesitt et al. |
| 5,997,555 | A | 12/1999 | Kontos | 7,316,704 B2 | 1/2008 | Bagaoisan et al. |
| 6,001,109 | A | 12/1999 | Kontos | 7,326,230 B2 | 2/2008 | Ravikumar |
| 6,022,372 | A | 2/2000 | Kontos | 7,331,979 B2 | 2/2008 | Khosravi et al. |
| 6,024,747 | A | 2/2000 | Kontos | 7,335,220 B2 | 2/2008 | Khosravi et al. |
| 6,036,699 | A | 3/2000 | Andreas et al. | 7,361,183 B2 | 4/2008 | Ginn |
| 6,042,601 | A | 3/2000 | Smith | 7,361,185 B2 | 4/2008 | O'Malley et al. |
| 6,048,351 | A | 4/2000 | Gordon et al. | 7,377,927 B2 | 5/2008 | Burdulis, Jr. et al. |
| 6,048,354 | A | 4/2000 | Lawrence | 7,390,328 B2 | 6/2008 | Modesitt |
| 6,048,357 | A | 4/2000 | Kontos | 7,393,363 B2 | 7/2008 | Ginn |
| 6,068,603 | A | 5/2000 | Suzuki | 7,442,198 B2 | 10/2008 | Gellman et al. |
| 6,077,276 | A | 6/2000 | Kontos | 7,445,626 B2 | 11/2008 | Songer et al. |
| 6,077,279 | A | 6/2000 | Kontos | 7,449,024 B2 | 11/2008 | Stafford |
| 6,117,144 | A | 9/2000 | Nobles et al. | 7,462,188 B2 | 12/2008 | McIntosh |
| 6,117,145 | A | 9/2000 | Wood et al. | 7,753,923 B2 | 7/2010 | St. Goar et al. |
| 6,126,675 | A | 10/2000 | Shchervinsky et al. | 7,837,696 B2 | 11/2010 | Modesitt et al. |
| 6,132,439 | A | 10/2000 | Kontos | 7,842,047 B2 | 11/2010 | Modesitt et al. |
| 6,132,440 | A | 10/2000 | Hathaway et al. | 7,842,048 B2 | 11/2010 | Ma |
| 6,136,010 | A | 10/2000 | Modesitt et al. | 7,842,049 B2 | 11/2010 | Voss |
| 6,139,556 | A | 10/2000 | Kontos | 7,846,170 B2 | 12/2010 | Modesitt et al. |
| 6,152,936 | A | 11/2000 | Christy et al. | 7,850,701 B2 | 12/2010 | Modesitt |
| 6,165,183 | A | 12/2000 | Kuehn et al. | 7,883,517 B2 | 2/2011 | Pantages et al. |
| 6,165,204 | A | 12/2000 | Levinson et al. | 2001/0046518 A1 | 11/2001 | Sawhney |
| 6,190,396 | B1 | 2/2001 | Whitin et al. | 2002/0045908 A1 | 4/2002 | Nobles et al. |
| 6,197,042 | B1 | 3/2001 | Ginn et al. | 2002/0095164 A1 | 7/2002 | Andreas et al. |
| 6,206,893 | B1 | 3/2001 | Klein et al. | 2002/0099389 A1 | 7/2002 | Michler et al. |
| 6,206,895 | B1 | 3/2001 | Levinson et al. | 2002/0106409 A1 | 8/2002 | Sawhney et al. |
| 6,245,079 | B1 | 6/2001 | Nobles et al. | 2002/0177876 A1 | 11/2002 | Roby et al. |
| 6,248,124 | B1 | 6/2001 | Pedros et al. | 2003/0093093 A1 | 5/2003 | Modesitt et al. |
| 6,296,657 | B1 | 10/2001 | Brucker | 2003/0195529 A1 | 10/2003 | Takamoto et al. |
| 6,348,059 | B1 | 2/2002 | Hathaway et al. | 2004/0009205 A1 | 1/2004 | Sawhney |
| 6,355,050 | B1 | 3/2002 | Andreas et al. | 2004/0092964 A1 | 5/2004 | Modesitt et al. |
| 6,358,258 | B1 | 3/2002 | Arcia et al. | 2004/0093027 A1 | 5/2004 | Fabisiak et al. |
| 6,395,015 | B1 | 5/2002 | Borst et al. | 2004/0097978 A1 | 5/2004 | Modesitt et al. |
| 6,428,472 | B1 | 8/2002 | Haas | 2004/0127940 A1 | 7/2004 | Ginn et al. |
| 6,428,549 | B1 * | 8/2002 | Kontos ..................... 606/144 | 2004/0143290 A1 | 7/2004 | Brightbill |
| 6,436,109 | B1 | 8/2002 | Kontos | 2004/0158127 A1 | 8/2004 | Okada |
| 6,443,963 | B1 | 9/2002 | Baldwin et al. | 2004/0158287 A1 | 8/2004 | Cragg et al. |
| 6,451,031 | B1 | 9/2002 | Kontos | 2004/0167511 A1 | 8/2004 | Buehlmann et al. |
| 6,511,489 | B2 | 1/2003 | Field et al. | 2004/0181238 A1 | 9/2004 | Zarbatany et al. |
| 6,517,553 | B2 | 2/2003 | Klein et al. | 2004/0186487 A1 | 9/2004 | Klein et al. |
| 6,533,812 | B2 | 3/2003 | Swanson et al. | 2004/0191277 A1 | 9/2004 | Sawhney et al. |
| 6,551,330 | B1 * | 4/2003 | Bain et al. ................ 606/144 | 2004/0215232 A1 | 10/2004 | Belhe et al. |
| 6,558,399 | B1 | 5/2003 | Isbell et al. | 2004/0225301 A1 | 11/2004 | Roop et al. |
| 6,562,052 | B2 | 5/2003 | Nobles et al. | 2004/0267193 A1 | 12/2004 | Bagaoisan et al. |
| 6,569,185 | B2 | 5/2003 | Ungs | 2004/0267308 A1 | 12/2004 | Bagaoisan et al. |
| 6,572,629 | B2 | 6/2003 | Kalloo et al. | 2005/0059982 A1 | 3/2005 | Zung et al. |
| 6,610,072 | B1 | 8/2003 | Christy et al. | 2005/0070923 A1 | 3/2005 | McIntosh |
| 6,623,509 | B2 | 9/2003 | Ginn | 2005/0075665 A1 | 4/2005 | Brenzel et al. |
| 6,623,510 | B2 | 9/2003 | Carley et al. | 2005/0085851 A1 | 4/2005 | Fiehler et al. |
| 6,632,237 | B2 | 10/2003 | Ben-David et al. | 2005/0085854 A1 | 4/2005 | Ginn |
| 6,641,592 | B1 | 11/2003 | Sauer et al. | 2005/0085855 A1 | 4/2005 | Forsberg |
| 6,663,655 | B2 | 12/2003 | Ginn et al. | 2005/0121042 A1 | 6/2005 | Belhe et al. |
| 6,676,685 | B2 | 1/2004 | Pedros et al. | 2005/0149117 A1 | 7/2005 | Khosravi et al. |
| 6,695,867 | B2 | 2/2004 | Ginn et al. | 2005/0177189 A1 | 8/2005 | Ginn et al. |
| 6,716,228 | B2 | 4/2004 | Tal | 2005/0222614 A1 | 10/2005 | Ginn et al. |
| 6,743,195 | B2 | 6/2004 | Zucker | 2005/0245876 A1 | 11/2005 | Khosravi et al. |
| 6,743,259 | B2 | 6/2004 | Ginn | 2005/0267528 A1 | 12/2005 | Ginn et al. |
| 6,749,621 | B2 | 6/2004 | Pantages et al. | 2005/0273137 A1 | 12/2005 | Ginn |
| 6,749,622 | B2 | 6/2004 | McGuckin, Jr. et al. | 2006/0034930 A1 | 2/2006 | Khosravi et al. |
| 6,837,906 | B2 | 1/2005 | Ginn | 2006/0047313 A1 | 3/2006 | Khanna et al. |
| 6,846,319 | B2 | 1/2005 | Ginn et al. | 2006/0079914 A1 * | 4/2006 | Modesitt et al. .............. 606/144 |
| 6,890,343 | B2 | 5/2005 | Ginn et al. | 2006/0100664 A1 | 5/2006 | Pai et al. |

| | | | |
|---|---|---|---|
| 2006/0167477 A1 | 7/2006 | Arcia et al. | |
| 2006/0173469 A1 | 8/2006 | Klein | |
| 2006/0253037 A1 | 11/2006 | Ginn et al. | |
| 2006/0253072 A1 | 11/2006 | Pai et al. | |
| 2007/0032798 A1 | 2/2007 | Pantages et al. | |
| 2007/0032801 A1 | 2/2007 | Pantages et al. | |
| 2007/0060950 A1 | 3/2007 | Khosravi et al. | |
| 2007/0123817 A1 | 5/2007 | Khosravi et al. | |
| 2007/0276410 A1 | 11/2007 | McIntosh | |
| 2007/0282354 A1 | 12/2007 | McIntosh | |
| 2008/0009794 A1 | 1/2008 | Bagaoisan et al. | |
| 2008/0065151 A1 | 3/2008 | Ginn | |
| 2008/0065152 A1 | 3/2008 | Carley | |
| 2008/0287967 A1 | 11/2008 | Andreas et al. | |
| 2008/0319458 A1 | 12/2008 | Reynolds | |
| 2009/0005793 A1 | 1/2009 | Pantages et al. | |
| 2009/0036906 A1 | 2/2009 | Stafford | |
| 2009/0048615 A1 | 2/2009 | McIntosh | |
| 2009/0088779 A1 | 4/2009 | Zung et al. | |
| 2009/0157105 A1 | 6/2009 | Zung et al. | |
| 2011/0066184 A1 | 3/2011 | Modesitt et al. | |
| 2011/0071472 A1 | 3/2011 | Voss | |
| 2011/0071552 A1 | 3/2011 | Ma | |
| 2011/0071567 A1 | 3/2011 | Modesitt et al. | |
| 2011/0077670 A1 | 3/2011 | Modesitt et al. | |
| 2012/0053600 A1 | 3/2012 | Fortson | |

FOREIGN PATENT DOCUMENTS

| | | |
|---|---|---|
| DE | 4210724 | 7/1993 |
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 01/35833 | 5/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/019016 | 2/2007 |
| WO | WO 2007/081836 | 7/2007 |

OTHER PUBLICATIONS

U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
Cardiac Catheterization and Angiography, 3rd Ed., Lea N. ad Febiger, Philadelphia, pp. 1-49, 52-247. 1986.
Cardio-Thoracic Systems Prospectus dated Mar. 20, 1996. pp. 1-4, 25-40.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintcchnik GmbH, Product Brochure entitled "REMA," Apr. 2001, 7 pages.
Serruys, PW et al., A Comparision of Balloon-Expandable-Stent Implantaion With Balloon Angioplasty in Patients With Coronary Artery Disease, New England Journal of Medicine, 331:489-495, 1994.
Taber's Cyclopedic Medical Dictionary, 18th Ed., p. 747, Feb. 1997.
U.S. Appl. No. 07/989,611, May 12, 1993, Office Action.
U.S. Appl. No. 07/989,611, Aug. 1, 1994, Office Action.
U.S/ Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.

U.S. Appl. No. 08/638,076, Jan. 21, 1997, Office Action.
U.S. Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999, Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/262,402, Mar. 29, 2000, Office Action.
U.S. Appl. No. 09/262,402, May 30, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/095,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.
U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.
U.S. Appl. No. 09/988,541, Dec. 13, 2005, Notice of Allowance.
U.S. Appl. No. 10/033,689, Sep. 30, 2003, Office Action.
U.S. Appl. No. 10/152,272, Jan. 24, 2005, Office Action.
U.S. Appl. No. 10/152,272, May 13, 2005, Notice of Allowance.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.
U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/357,984, Jan. 9, 2006, Office Action.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007,Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/660,288, Apr. 29, 2009, Office Action.
U.S. Appl. No. 10/660,288, Aug. 3, 2009, Office Action.
U.S. Appl. No. 10/660,288, Mar. 30, 2010, Office Action.
U.S. Appl. No. 10/660,288, Mar. 29, 2011, Office Action.
U.S. Appl. No. 10/729,541, Dec. 12, 2006, Office Action.
U.S. Appl. No. 10/729,541, Jun. 18, 2007, Office Action.
U.S. Appl. No. 10/729,541, Jan. 8, 2008,Office Action.
U.S. Appl. No. 10/729,541, Sep. 23, 2008, Office Action.
U.S. Appl. No. 10/729,541, May 1, 2009, Office Action.
U.S. Appl. No. 10/729,541, Nov. 16, 2009, Notice of Allowance.
U.S. Appl. No. 10/729,541, Mar. 25, 2010,Notice of Allowance.
U.S. Appl. No. 10/729,541, Jul. 12, 2010, Notice of Allowance.
U.S. Appl. No. 10/729,541, Nov. 3, 2010, Issue Notification.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.
U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,531, Feb. 9, 2009, Office Action.
U.S. Appl. No. 10/909,531, Sep. 16, 2009, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 10/909,531, Nov. 23, 2010, Issue Notification.
U.S. Appl. No. 10/948,445, Jul. 11, 2007, Office Action.
U.S.Appl. No. 11/199,338, Jan. 25, 2007, Office Action.
U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2010, Notice of Allowance.
U.S. Appl. No. 11/199,515, Aug. 2, 2010, Notice of Allowance.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/273,107, Oct. 28, 2009, Office Action.
U.S. Appl. No. 11/273,107, Jun. 2, 2010, Office Action.
U.S. Appl. No. 11/273,107, Oct. 27, 2010, Office Action.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.
U.S. Appl. No. 11/363,005, Dec. 23, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/363,005, Jul. 23, 2010, Notice of Allowance.
U.S. Appl. No. 11/363,005, Nov. 10, 2010, Issue Notification.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/465,527, Nov. 10, 2010, Issue Notification.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/552,593, Mar. 22, 2010, Notice of Allowance.
U.S. Appl. No. 11/552,593, Jul. 22, 2010, Notice of Allowance.
U.S. Appl. No. 11/552,593, Nov. 10, 2010, Issue Notification.
U.S. Appl. No. 11/688,722, Mar. 10, 2010, Office Action.

U.S. Appl. No. 11/688,722, Jul. 29, 2010, Notice of Allowance.
U.S. Appl. No. 11/688,722, Nov. 17, 2010, Issue Notification.
U.S. Appl. No. 11/891,358, Apr. 26, 2010, Office Action.
U.S. Appl. No. 11/891,358, Oct. 19, 2010, Office Action.
U.S. Appl. No. 11/891,513, Apr. 9, 2010, Office Action.
U.S. Appl. No. 11/891,513, Sep. 28, 2010, Office Action.
U.S. Appl. No. 11/960,593, Sep. 14, 2010, Office Action.
U.S. Appl. No. 11/960,593, Nov. 3, 2010, Office Action.
U.S. Appl. No. 12/182,836, Oct. 5, 2010, Office Action.
U.S. Appl. No. 12/257,127, Aug. 30, 2010, Office Action.
U.S. Appl. No. 12/257,127, Dec. 22, 2010, Office Action.
U.S. Appl. No. 12/334,077, Oct. 27, 2010, Office Action.
U.S. Appl. No. 12/334,085, Dec. 23, 2010, Office Action.
U.S. Appl. No. 90/006,469, Nov. 29, 2002, Request for Re-Examination.
U.S. Appl. No. 90/006,469, Sep. 10, 2004, Office Action.
U.S. Appl. No. 90/006,469, Sep. 27, 2005, Notice of Re-Issue.
U.S. Appl. No. 90/006,469, Jun. 27, 2006, Re-Examination Certification.
U.S. Appl. No. 11/199,496, Apr. 28, 2011, Office Action.
U.S. Appl. No. 11/960,593, Apr. 28, 2011, Office Action.
U.S. Appl. No. 11/273,107, Jun. 2, 2011, Notice of Allowance.
U.S. Appl. No. 12/950,338, Jun. 15, 2011, Office Action.
U.S. Appl. No. 12/182,836, Jun. 23, 2011, Office Action.
U.S. Appl. No. 12/966,961, Oct. 26, 2011, Issue Notification.
U.S. Appl. No. 11/891,358, Nov. 18, 2011, Notice of Allowance.
U.S. Appl. No. 12/955,848, Nov. 15, 201, Office Action.
U.S. Appl. No. 12/955,848, Jun. 30, 2011, Office Action.
U.S. Appl. No. 10/660,288, Sep. 30, 2011, Notice of Allowance.
U.S. Appl. No. 11/273,107, Sep. 28, 2011, Issue Notification.
U.S. Appl. No. 12/961,239, Oct. 12, 2011, Issue Notification.
U.S. Appl. No. 12/334,085, Jan. 9, 2012, Notice of Allowance.
U.S. Appl. No. 12/955,863, Jan. 6, 2012, Office Action.
U.S. Appl. No. 12/257,127, Jan. 12, 2012, Office Action.
U.S. Appl. No. 10/660,288, Feb. 29, 2012, Issue Notification.
U.S. Appl. No. 11/997,379, Feb. 28, 2012, Office Action.
U.S. Appl. No. 12/247,012, Mar. 16, 2012, Office Action,
U.S. Appl. No. 12/955,869, Mar. 22, 2012, Notice of Allowance.
U.S. Appl. No. 11/891,513, Nov. 1, 2011, Notice of Allowance.
U.S. Appl. No. 12/950,338, Nov. 1, 2011, Notice of Allowance.
U.S. Appl. No. 12/955,869, Oct. 18, 2011, Office Action.
U.S. Appl. No. 11/199,496, Aug. 18, 2011, Notice of Allowance.
U.S. Appl. No. 11/891,358, Aug. 31, 2011, Office Action.
U.S. Appl. No. 11/891,513, Aug. 31, 2011, Office action.
U.S. Appl. No. 11/997,379, Jul. 13, 2011, Office Action.
U.S. Appl. No. 12/257,127, Jul. 6, 2011, Office Action.
U.S. Appl. No. 12/334,077, Jul. 21, 2011, Office Action.
U.S. Appl. No. 12/334,085, Aug. 4, 2011, Office Action.
U.S. Appl. No. 12/961,239, Jul. 26, 2011, Notice of Allowance.
U.S. Appl. No. 12/966,961, Aug. 18, 2011, Notice of Allowance.
U.S. Appl. No. 12/247,012, Oct. 13, 2011, Office Action.
U.S. Appl. No. 11/891,513, mailed Aug. 15, 2012, Issue Notification.
U.S. Appl. No. 12/247,012, mailed Aug. 13, 2012, Notice of Allowance.
U.S. Appl. No. 12/950,338, mailed Aug. 8, 2012, Notice of Allowance.
U.S. Appl. No. 12/955,863, mailed Aug. 8, 2012, Issue Notification.
U.S. Appl. No. 11/997,379, mailed Aug. 29, 2012, Issue Notification.
U.S. Appl. No. 12/873,728, mailed Sep. 11, 2012, Office Action.

* cited by examiner

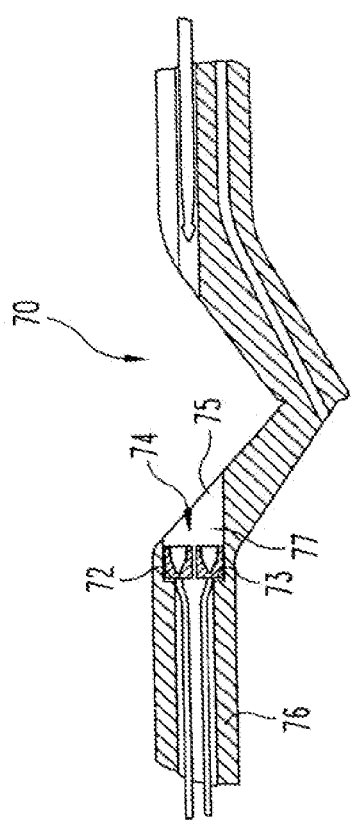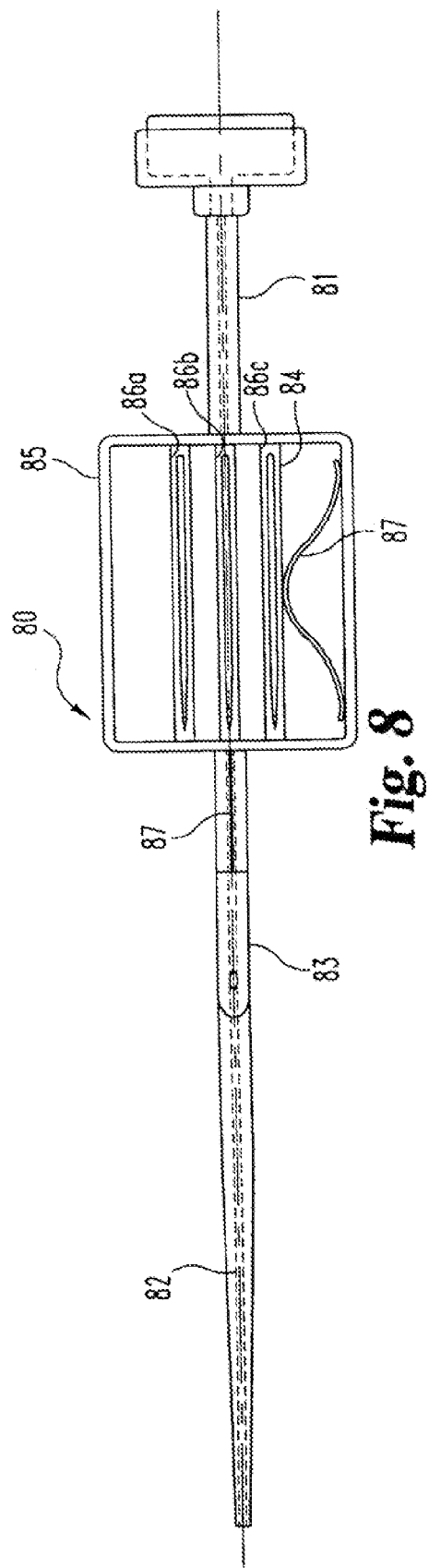

VASCULAR SUTURING DEVICE

CROSS REFERENCE TO RELATED APPLICATIONS

This application is a divisional of U.S. application Ser. No. 11/199,515, filed Aug. 8, 2005, now U.S. Pat. No. 7,883,517, which is hereby incorporated by reference in its entirety.

BACKGROUND OF THE INVENTION

The present invention generally relates to surgical instruments and methods of suturing tissue.

A number of diagnostic and treatment procedures are conducted intravascularly. Typically, a catheter is introduced into the vascular system at a convenient access location and is then guided to the target treatment site. The Seldinger Technique is one of the well-known early examples of this type of procedure which can include catheterization and angioplasty techniques. Procedures such as this require a vascular access. Typically an introducer sheath with or without a guide wire is inserted through a puncture wound in a vessel such as the femoral artery at a location near the groin. A catheter and other instrumentation can then be inserted through the sheath and guided to the targeted treatment site. After the diagnostic and/or treatment procedure has been completed, the puncture wound must be closed. Closing the wound can be difficult because of the substantial bleeding that can occur through an open wound in the vascular vessel. One technique for hemostasis includes applying pressure near or upstream of the puncture site. This approach suffers from many deleterious effects, not the least of which are that it can be time consuming and extremely uncomfortable—even painful—for the patient because the pressure is applied directly on or adjacent to the traumatized site. Frequently anticoagulants are employed for the original diagnostic/treatment procedures. This delays clot formation during the procedure, and this effect lasts through the initial recovery period, lengthening the time during which pressure must be applied to the wound for up to twelve hours or more. During this initial recovery period, it is imperative that the patient remain still, further adding to the patient's discomfort.

Alternatively, the puncture wound can be closed with sutures. This can be extremely difficult because the vascular vessel with the puncture lies underneath the patient's outer skin. Some vascular vessels, notably the femoral artery, appear to be relatively large; however, in practice, even the largest arteries cannot be readily sutured. Therefore, devices have been developed to facilitate subcutaneous suturing of arteries and veins. These devices can extend through the outer tissue to the puncture wound in the vascular vessel. Needles are then deployed from the device to suture the tissue adjacent the puncture wound.

Certain devices are inserted subcutaneously into the puncture wound. One or more needles are deployed to pierce the tissue in a direction from the exterior to the interior of the vascular vessel. The needles continue to be advanced into a depository in the portion of the device located within the lumen of the vessel. The suturing device can be removed from the vessel (and the patient) by withdrawing the needles and suture material at the same time. These devices leave an inverted suture path after completion of the closure. The suture material runs from the exterior tissue surrounding the puncture wound back up through the wound itself which is then tied off. Some complications may arise resulting from this type of closure, including oozing, excessive bleeding, and, on rare occasions, knot loosening. It would be preferred to provide a suturing device that allows the suture path to extend across the puncture opening internal of the vessel membrane with the suture knot overlying the exterior of the closed wound.

In view of the above background, there remains a need for improved and/or alternative methods and devices for closing the vascular opening or punctures. The present invention is addressed to these needs.

SUMMARY OF THE INVENTION

The present invention relates to suturing devices and the use thereof. Various aspects of the invention are novel, non-obvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a suturing device for suturing an opening in a vascular vessel. The device comprises a proximal member that can be configured as an elongate body with a needle channel extending at least partway therethrough and sized to receive at least one needle; a distal member configured to be inserted within a lumen of a vascular vessel, where the distal member has a receptacle located therein and a length of suture material with a needle engaging fitting positioned in the receptacle; and an intermediate member disposed between the proximal member and the distal member. In one embodiment, the intermediate member defines a tissue receiving area and has a first opening providing a passageway to the channel and a second opening providing a passageway into the receptacle. In other embodiments, the distal member defines a substantially linear longitudinal axis and the intermediate member can deviate from that longitudinal axis. In other embodiments, the intermediate defines a tissue receiving area that provides a linear needle pathway through the tissue receiving area.

In another form, the present invention provides a suturing device for suturing an opening in a vascular vessel. The suturing device comprises: a proximal member including an elongate body having a needle channel therethrough sized to receive at least one needle and including a needle cartridge slidably mounted thereon configured to contain two or more needles; a distal member configured to be inserted within a lumen of a vascular vessel and having a receptacle located therein and a length of suture material with a needle engaging fitting positioned in the receptacle; an intermediate member disposed between the proximal member and the distal member, where the intermediate member defines a tissue receiving area and has a first opening providing a passageway to the channel and a second opening providing a passageway into the receptacle. and a length of suture material comprising a needle engaging fitting positioned in the receptacle to engage a needle entering from the second opening.

In yet another form, the present invention provides A method of suturing an opening in a vascular vessel, said method comprising: inserting a vascular suturing device through the opening in the vascular vessel, said suturing device comprising a proximal member having a needle channel and a needle therein; a distal member configured to be inserted into the lumen of the vascular vessel, the distal member having a cavity therein and a length of suture material disposed in the cavity; and a connecting member between the proximal and distal members, the connecting member angled or curved to offset the channel and the cavity from the opening in the vascular vessel and having a first opening into the needle channel and a second opening into the cavity; sufficiently advancing the needle through the needle channel to pierce a portion of tissue adjacent the opening in the vessel and extend into the cavity of the distal member; and capturing the suture within the cavity with the needle; and retracting the needle carrying a first portion of the suture back through the tissue and the channel.

BRIEF DESCRIPTION OF THE DRAWINGS

FIG. 1A is an illustration of suture material suitable for use in the suturing device of FIG. 1 accordance with the present invention.

FIG. 7 is an enlarged cross-sectional view of an alternative embodiment of a connector member with suture material and two laterally disposed ferrules in accordance with the present invention.

FIG. 8 is a perspective view of an alternative embodiment of a suturing device with a needle cartridge for use in accordance with the present invention.

DETAILED DESCRIPTION OF THE INVENTION

Figure 1:
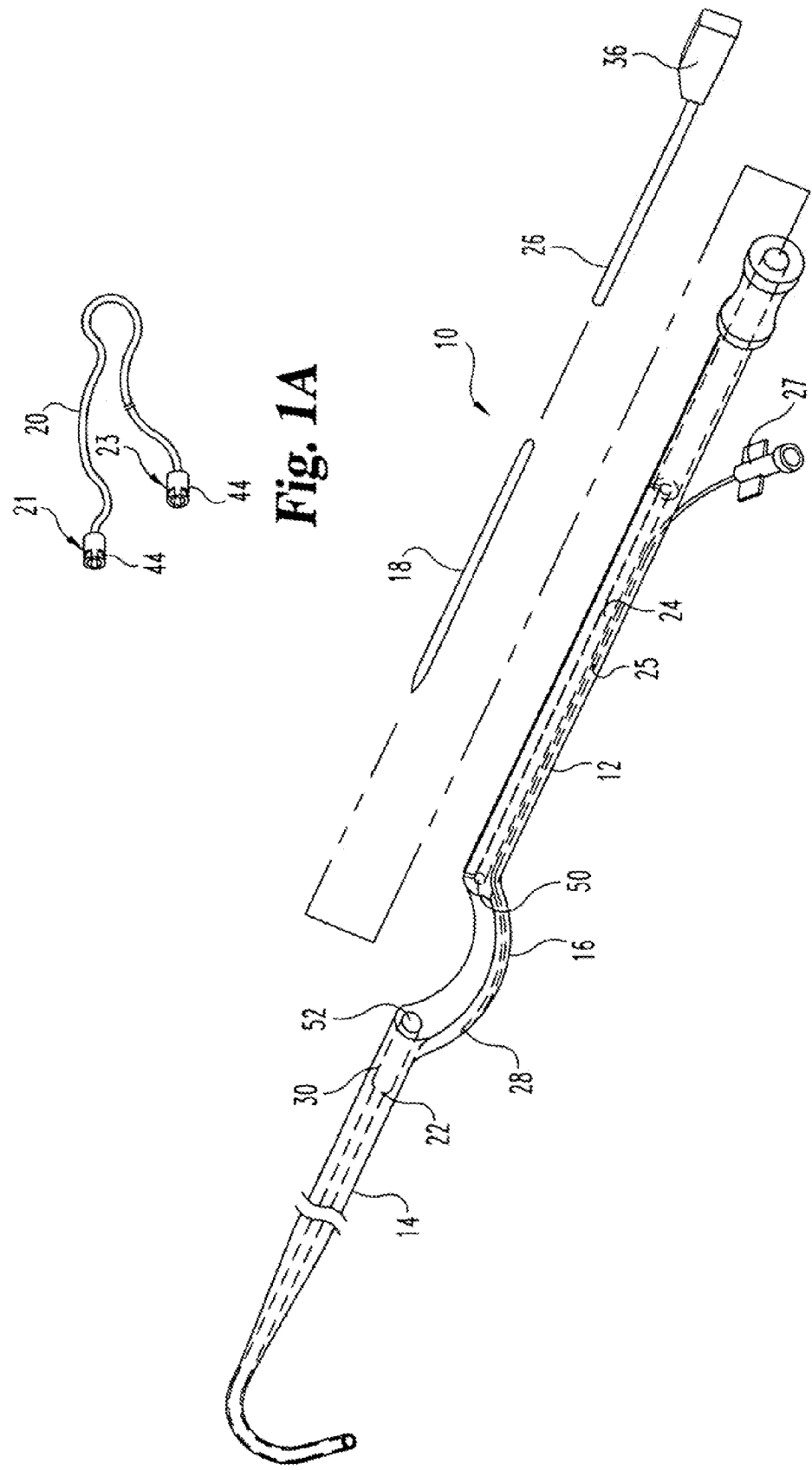
FIG. 1 is an exploded view of one embodiment of a suturing device in accordance with the present invention.

FIG. 1 is an exploded view of one embodiment of a suturing device 10 for suturing vascular vessels in accordance with the present invention. Device 10 includes a proximal member 12, a distal member 14, and an intermediate member 16 located therebetween. Device 10 includes one or more needles 18 advanceable through a portion of the proximal and distal members. A needle pusher 26 can either push or engage needle 18 to advance it through a channel 24 in the proximal member and through vascular tissue adjacent the puncture wound. In one form, suture material can be attached to needle 18 which is then advanced in a distal direction through tissue. In other forms, suture material can be located within distal member to be snared by a needle to be withdrawn in a proximal direction through tissue. A second needle and subsequent needles can be similarly configured and manipulated to place sutures through tissue adjacent a puncture wound in a vascular vessel. The suture material(s) threaded through the vascular tissue can be drawn taut closing the puncture wound. A surgical knot or other suture securing device can complete the wound closure.

As used herein, the term "proximal" refers to a direction toward the surgeon and away from the patient or a location closer to the surgeon, while the term "distal" refers to a direction towards the patient and away from the surgeon or a location closer to the patient.

Proximal member 12 is provided as an elongated portion with a substantially cylindrical or oval radial cross section. Member 12 includes a first end of sufficient dimensions to be readily grasped by the surgeon to manipulate the device during the procedures. Proximal member 12 can also include a gripping portion to facilitate handling during the surgical procedure. Needle channel 24 runs longitudinally along at least a portion of proximal member. In one embodiment, channel 24 extends along the entire length of proximal member from a first end positioned proximal to the surgeon to a second end adjacent to intermediate member 16. In this embodiment, one or more needle(s) 18 and needle pusher(s) 26 can be inserted into and retrieved from channel 24 at the first end. In other embodiments, channel 24 extends only partly through the proximal member 12. Needle channel 24 can be centrally located along proximal member 12. In preferred embodiments, proximal member 12 includes a single needle channel 24 through which one, two, three, or more needles can be advanced. Alleviating multiple needle channels within the suturing device provides a more compact member, which can be particularly advantageous for subcutaneous procedures.

Channel 24 is sized and dimensioned to allow one or more needles 18 to be advanceable therethrough and into vascular tissue around the puncture wound. Furthermore, channel 24 can be either partly or completely encased within the body of proximal member 12. However, in a preferred embodiment, channel 24 is not encased within the body of proximal member 12. Rather, channel 24 is provided as a slot formed into the surface of proximal member 12. Preferably the slot is configured to retain one or more needles within the slot. For example, the slot can be formed to have an opening at the exterior surface of proximal member that is narrower than the diameter of the needles (and optionally the pusher) while the internal portion or diameter of the slot can be dimensioned to permit facile movement of the needle therethrough. An exit opening is located at the distal end of channel 24.

Proximal member 12 includes a blood return line or lumen 25 that terminates in a fitting 27, for example, a luer lock that can be mated to a syringe. Alternatively, blood return lumen 25 can terminate in a valve or shunt to control and stop blood flow therethrough. It is preferable that blood return lumen 25 be transparent to allow visible observation of blood originating from inside the vascular vessel. This can facilitate proper placement of the device for suturing.

Distal member 14 is sized and/or configured to be received within an opening or wound leading to a lumen of a patient's vascular vessel. Therefore, it is preferable that at least distal member 14 be formed of a flexible or elastomeric material that is biocompatible—particularly with blood. In a preferred embodiment, proximal member 12 and distal member 14 define a longitudinal axis. In additional embodiments, distal member 14 can be coated or impregnated with a lubricant, bioactive agent, such as an anticoagulant material, and the like. In certain embodiments, distal member 14 is composed of a biocompatible polymeric material commonly used for catheters, such as silicone rubber, polyolefin polyurethane, polytetrafluoroethylene, and the like.

FIG. 1A illustrates one or more lengths of suture material 20 that can be included in receptacle 22 of distal member 14 in accordance with one embodiment of the present invention. The lengths of suture material 20 can include one or more fittings 21, 23, for example, a ferrule or cuff of porous or mesh material, to engage the needle.

Figure 2:
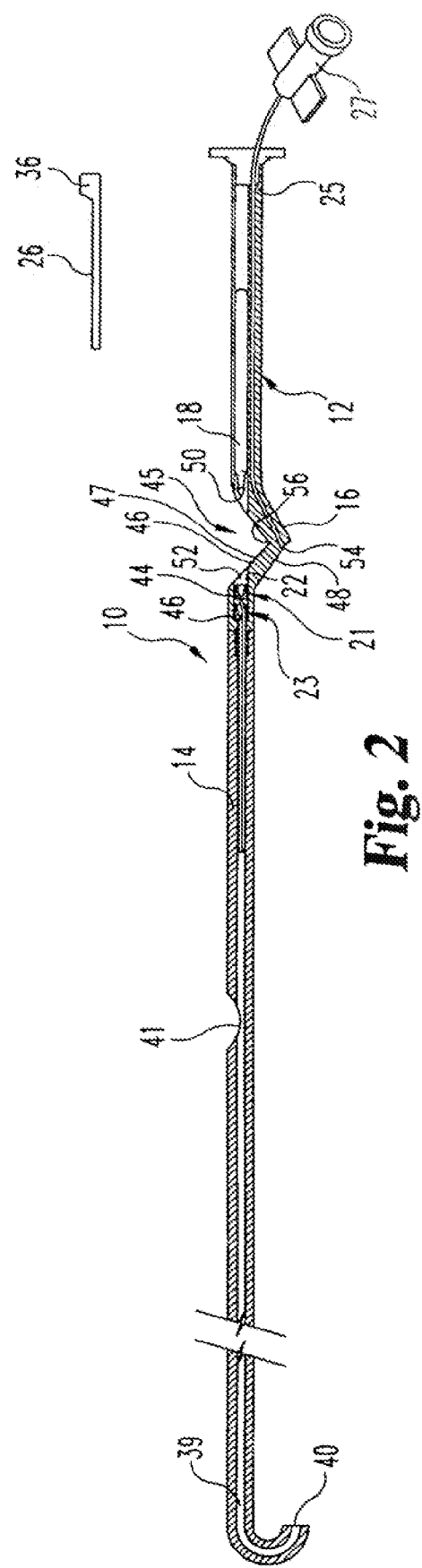
FIG. 2 is a cross-sectional view of the suturing device of FIG. 1 including the suture material of FIG. 1A.

Distal member 14 includes a receptacle 22. Receptacle 22 is sized to receive at least one length of suture material 20 with a corresponding fitting 21, as specifically shown in FIG. 2. Preferably receptacle 22 is sized to hold one, two, or more separate lengths of suture material. Each length of suture material can include either a single fitting 21 or two fittings—one on each end. In a preferred embodiment, receptacle 22 is provided as a multi-stage or tapered recess. Each fitting is positioned within a receptacle to allow for ready deployment and subsequent engagement with needle 18 advancing from channel 24 in proximal member 12. Preferably the fittings are releasably retained so that needles advancing into receptacle 22 can sequentially engage the fittings without forcing that fitting distally further or deeper into the receptacle. In one form, this can include a shoulder or abutment 30 extending from the internal wall of receptacle 22 to abut a distal end of a fitting. In other embodiments, this can include configuring the internal dimensions of receptacle 22 to taper or decrease in diameter in the distal direction. In other embodiments, a multi-stage receptacle 22 or stepped internal walls receptacle 22 can prevent movement of the fittings in the distal direction. In still other embodiments, the fittings are loaded within the receptacle 22 to bear against the suture material which is packed within the end of receptacle 22. In this embodiment, the bulk of suture material in receptacle 22 can inhibit or prevent distal movement of the fittings upon initial engagement with needle 18.

Figure 3:
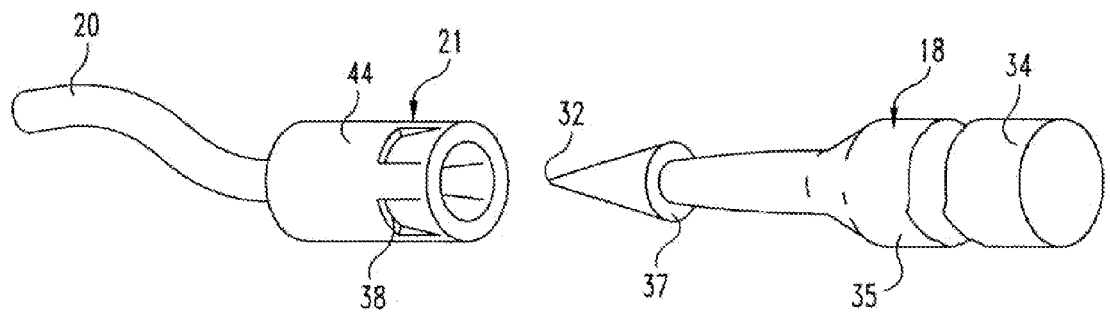
FIG. 3 is a perspective view of a ferrule and a needle for use with the suturing device in accordance with the present invention.
Figure 4:
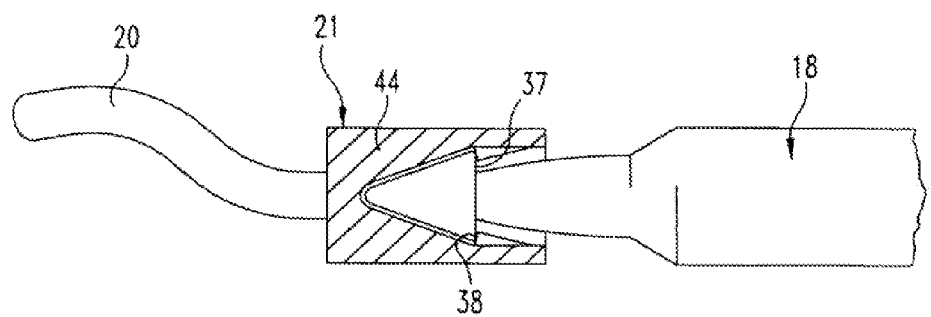
FIG. 4 is a cross-sectional view of the ferrule engaged with the needle of FIG. 3.

FIGS. 3 and 4 illustrate a portion of needle 18 and fitting 21 in the form of a ferrule 44. Needle 18 includes a distal tip 32 and a proximal end 34. Distal tip 32 is configured as a tissue piercing point or a barbed tip. Needle 18 is configured to grab suture material located in the lumen of the vessel and withdraw the suture material through vascular tissue. In the preferred embodiment, distal tip 32 is configured to securely engage with ferrule 44 which, in turn, is attached to a length of suture. Ferrule 44 can be extremely small, having roughly a diameter similar to or slightly larger than that of the suture material 20. Alternatively, ferrule 44 can have approximately the same diameter as the diameter of needle shaft 35. In this embodiment, distal tip 32 has a smaller diameter to allow it to be received inside ferrule 44. Distal needle tip 32 includes at least one recessed engagement surface or shoulder 37 configured to matingly engage with a corresponding engagement surface 38 provided on or in ferrule 44. In one form, the engagement surface is a tab extending into the interior of ferrule 44. In other embodiments, the engagement surface is a shoulder extending radially inward in ferrule 44 or a groove partly or completely encircling an interior wall of ferrule 44. Fitting 23 also may be in the form of a ferrule 46 shown in FIGS. 5 and 6. Ferrule 46 may have similar needle retention features.

Figure 5:
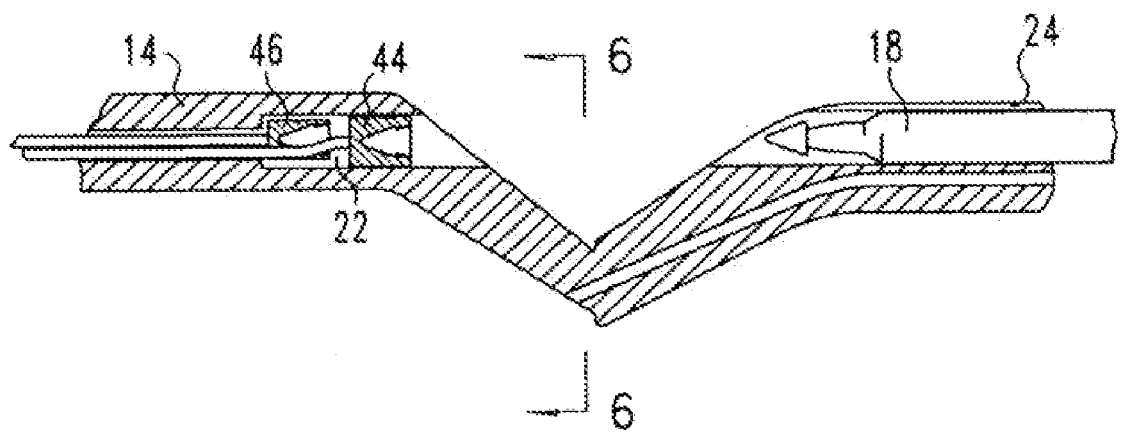
FIG. 5 is an enlarged, cross-sectional view of the intermediate member of the suturing device of FIG. 1 with the suture material of FIG. 1A.
Figure 6:
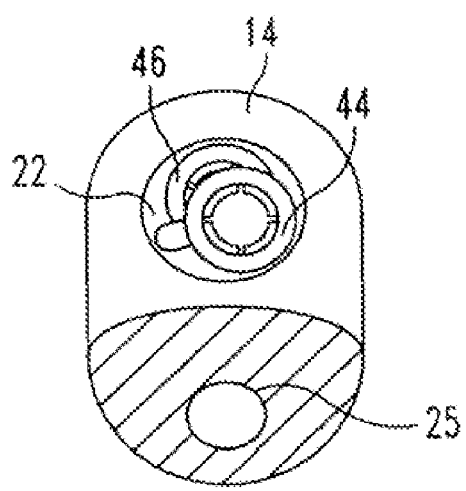
FIG. 6 is a radial cross-sectional view taken along section line 6-6 of the intermediate member illustrated in FIG. 5.
Figure 9:
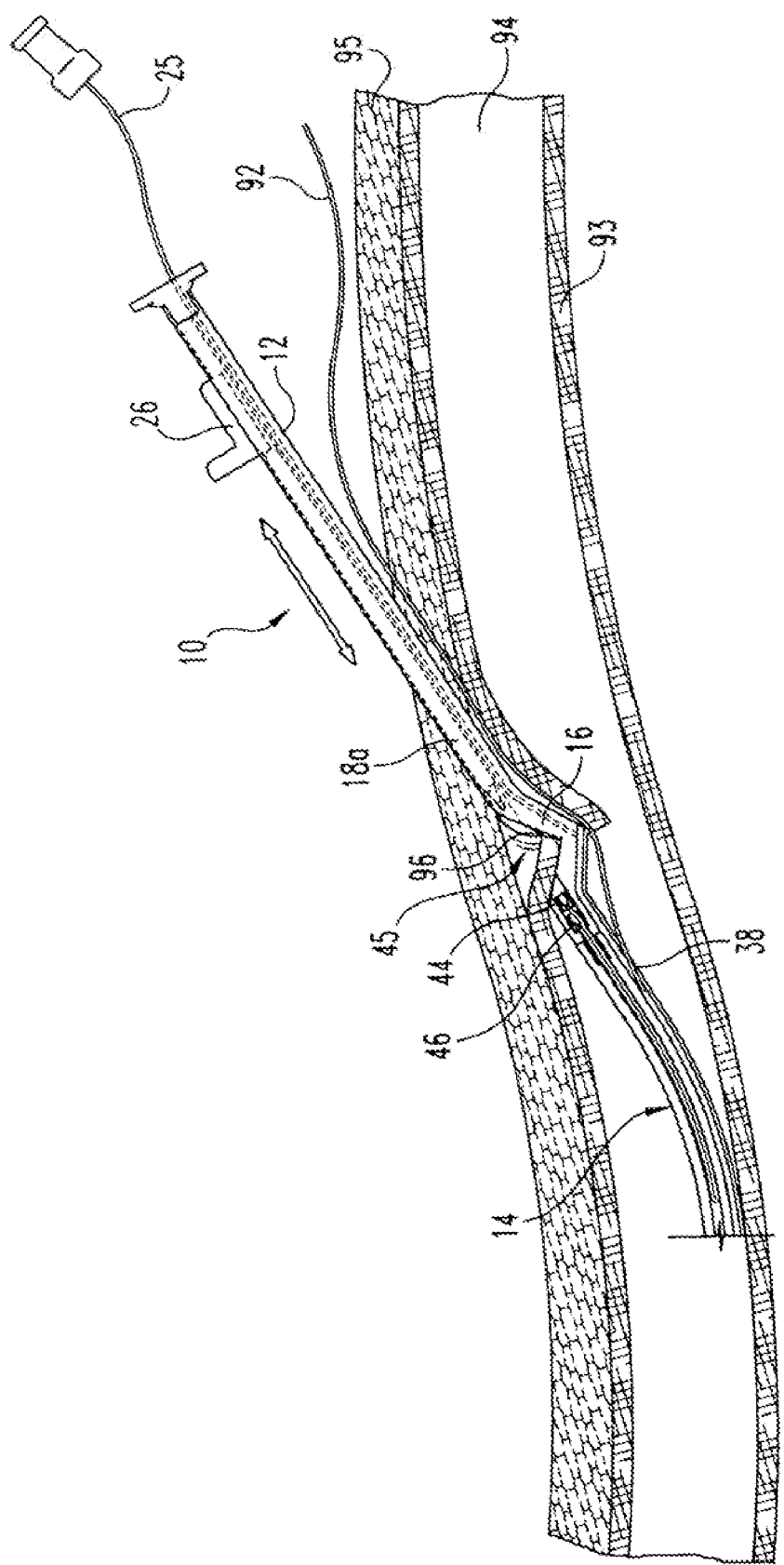
FIGS. 9-16 illustrate the use of the suturing device of FIG. 1 to suture vascular tissue.

FIGS. 5 and 6 show that the ferrules 44 and 46 need not be the same size—particularly the same diameter. In this regard certain advantages can be gained by providing the proximally located ferrule 44 with a diameter greater than that of the distally located ferrule 46. For example, this will allow sufficient room for the suture material extending from ferrule 44 to extend along side of ferrule 46—between ferrule 46 and an internal wall section of receptacle 22. In other considerations, the suture material from the proximally located ferrule 44 can be disposed between that ferrule and the next distally located ferrule 46. Ferrules 44 and 46 can also be tapered or "streamlined" to allow them to be readily pulled through a small needle puncture site in tissue as described below.

In one embodiment, the length of suture material which is attached to the different ferrules on each end can include different color codings for the different ends. This allows a surgeon to differentiate which sutures are attached to which ferrules to facilitate tying suitable knots to close puncture 96 in the vessel.

One or more of needles 18 and ferrules 44, 46 for use in the present invention can be provided as substantially described in U.S. Pat. No. 6,136,010 issued to Modesitt et al. and/or U.S. Pat. No. 6,368,334 issued to Sauer, which are incorporated herein by reference in their entirety.

Proximal end 34 of needle 18 can be free and configured to be handled by a surgeon. Alternatively, proximal end 34 can be engageable or secured to a needle pusher 26 shown in FIG. 2. In yet another embodiment, proximal end 34 can be integral or formed as a single unit with needle pusher 26. In either embodiment, needle pusher 26 is sized to be positioned within channel 24 and can further include a projection 36 to allow the surgeon to advance the needle pusher/needle combination along channel 24. In a preferred embodiment, needle pusher 26 is configured such that the surgeon can sequentially advance needle 18 in a proximal direction towards the patient and in a distal direction away from the patient.

Referring back to FIG. 2, distal member 14 can also include a lumen 39 extending at least partially therethrough. Preferably, lumen 39 is separate from receptacle 22. Lumen 39 can be provided to receive or follow a guide wire left in place after a particular diagnostic or treatment procedure. This can allow the facile insertion of distal member 14 into the patient's vascular vessel. In a preferred embodiment, an opening 40 receives a guide wire (not shown) that extends through lumen 39 and exits through a side opening 41 of distal member 14 to permit the guide wire to extend out without interfering with the needles, needle path, or suture material. The guide wire can be removed after placement of the suture device or left in as desired or considered medically prudent by the surgeon.

Intermediate member 16 is located between proximal member 12 and distal member 14. Intermediate member 16 defines a tissue-receiving area 45. In the illustrated embodiment, intermediate member is configured to include an arcuate portion or a crooked section. The arcuate portion or crook thus defines a concave interior surface 47 and a convex exterior surface 48. Intermediate member 16 includes a first opening 50 providing access from the channel 24 to the tissue receiving area 45 and a second opening 52 from the receptacle 22 providing to the tissue receiving area 45. Preferably, first and second openings 50 and 52 are linearly or axially aligned. Intermediate member 16 can be composed of a biocompatible material that is substantially resistant to deformation and therefore can maintain the linearity between channel 24 and receptacle/chamber 22 and the respective first and second openings 50 and 52. Examples of suitable materials include TEFLON, NYLON, polyamids, and the like.

Intermediate member 16 also includes means and structure for reliable positioning of the device during surgery to facilitate closing the vascular puncture wound with sutures. Part of the positioning structure includes an opening 54 providing fluid communication to blood return lumen 25 in proximal member 12. In a preferred embodiment, opening 54 is located on a portion of the convex surface of the crook opposite the tissue receiving area 45. When the distal member 14 of the device is suitably positioned within the lumen of a vascular vessel, opening 54 is also located in the interior of the lumen. This permits blood from the vessel to enter blood return lumen 25, which can then be visibly observed by the surgeon. If blood is not observed in blood return lumen 25, then the distal member may not have been inserted to a sufficient depth into the lumen of the vascular vessel.

Additionally, a ridge or stop 56 extends from the concave surface into the tissue receiving region. Stop 56 is configured to bear against vascular tissue adjacent the puncture wound. In a preferred embodiment, first opening 50 is adjacent stop 56 permitting needle 18 to pierce tissue adjacent thereto. Stop 56 is sized to bear against the vascular tissue and avert further insertion of the device 10 into the vascular vessel. When provided together, stop 56 and opening 50 with blood return lumen 25 cooperate to ensure accurate placement of the suturing device in the patient's vascular vessel. Ridge or stop 56 can also extend radially about the entire circumference of intermediate member 16.

FIG. 7 is a cross-sectional view of an intermediate member 70 of an alternative embodiment of a suture device. In this embodiment, fittings 72 and 73 are positioned radially or laterally displaced from each other in receptacle 74. A first fitting 72 is positioned axially aligned with second opening 75 in the distal member 76. A biasing element such as a leaf spring 77 can also be positioned in receptacle 74 to urge second fitting 73 into axial alignment with opening 75 once first fitting 72 has been displaced. Biasing element 77 can be a leaf spring as illustrated, an elastomeric projection, or other known biasing material suitable to urge fitting 72 into alignment as desired.

FIG. 8 is a perspective view of another embodiment of a suturing device 80 with a needle cartridge in accordance with the present invention. Device 80 includes a proximal member 81, a distal member 82, and an intermediate member 83 therebetween. Proximal member 81 includes a needle cartridge 84 slidably mounted in body 85. Needle cartridge 84 can include a plurality of needle slots, for example one, two, three, or more slots 86a. 86b, 86c . . . , each for a separate needle. Typically, the number of needles in needle cartridge 84 will coincide with the number of fittings with suture material in the receptacle in distal member 82. Each needle in needle cartridge 84 is individually advanceable through a central needle channel 87 along a length of proximal member 81. Needle cartridge 84 is laterally displacable within body 85 to axially align the selected needle slot 86a. 86b, 86c . . . with a single needle channel. If desired, needle cartridge can be biased to automatically align the successive needle slots with the needle channel after the preceding needle has been advanced along the channel. Alternatively, suturing device 80, body 120, and/or cartridge 118 can include one or more of ratchetings, positive stops, or locks to individually align the desired needle slot with the channel. In other embodiments, needle cartridge 84 can be provided as a revolving barrel that can hold two, three, or more needles in respective needle slots radially disposed about the barrel. The barrel can be rotatably mounted on or about proximal member 81. Distal member 82 and intermediate member 83 can be configured substantially as described above for members 14 and 16, respectively.

Referring to FIGS. 9 through 14, use of the suturing device 10, will now be described. A puncture wound in a vascular vessel can be sutured closed using the suturing device 10. Suturing device 10 can be inserted distally into the vascular vessel. This can be accomplished with or without the use of a guide wire. In a procedure where a guide wire has been previously used, suturing device 10 can be threaded onto a guide wire 92 which extends from internal vessel lumen 94 through a puncture wound 96 in vessel 93 and through a portion of the overlying tissue 95 to be exposed to the surgeon. In that regard, side opening 41 of lumen 39 can be threaded onto guide wire 92 which then extends out through opening 40. Thus, the flexible portion of distal member 14 can be gingerly threaded into the lumen 94 of vessel 93. The distal member 14 of device 10 can be positioned within lumen 94 such that intermediate member 16 engages with a portion of the tissue surrounding puncture 96. Distal member 14 is advanced in a distal direction until blood is observed in blood return lumen 25. Additionally, when provided, stop 56 abuts or bears against the external surface of the vascular vessel. This can be detected by the increased resistance to further advancement of the device in the distal direction. Both blood return lumen 25 and stop 56 can be used to ascertain that the device has been correctly positioned within the lumen 94 of the vascular vessel 93 to allow suturing of puncture 96. It should be noted that observance of blood in needle channel 24 is an indication that device 10 has been inserted too far into the lumen such that first opening 50 is exposed to the interior or blood side of vessel 93. If desired, guide wire 92 can then be withdrawn from lumen 39 and out of vascular vessel 93—if it is no longer needed for subsequent procedures.

After the distal member 14 is positioned as desired, the vascular tissue adjacent the puncture wound is received within the tissue receiving area 45. As noted above, intermediate member 16 provides an essentially linear needle pathway between channel 24, receptacle 22, and the vascular tissue in the tissue receiving area 45. Consequently, when needle 18 is advanced through channel 24, it pierces the vascular tissue at a first suture site 97 adjacent the puncture wound 96.

Figure 10:
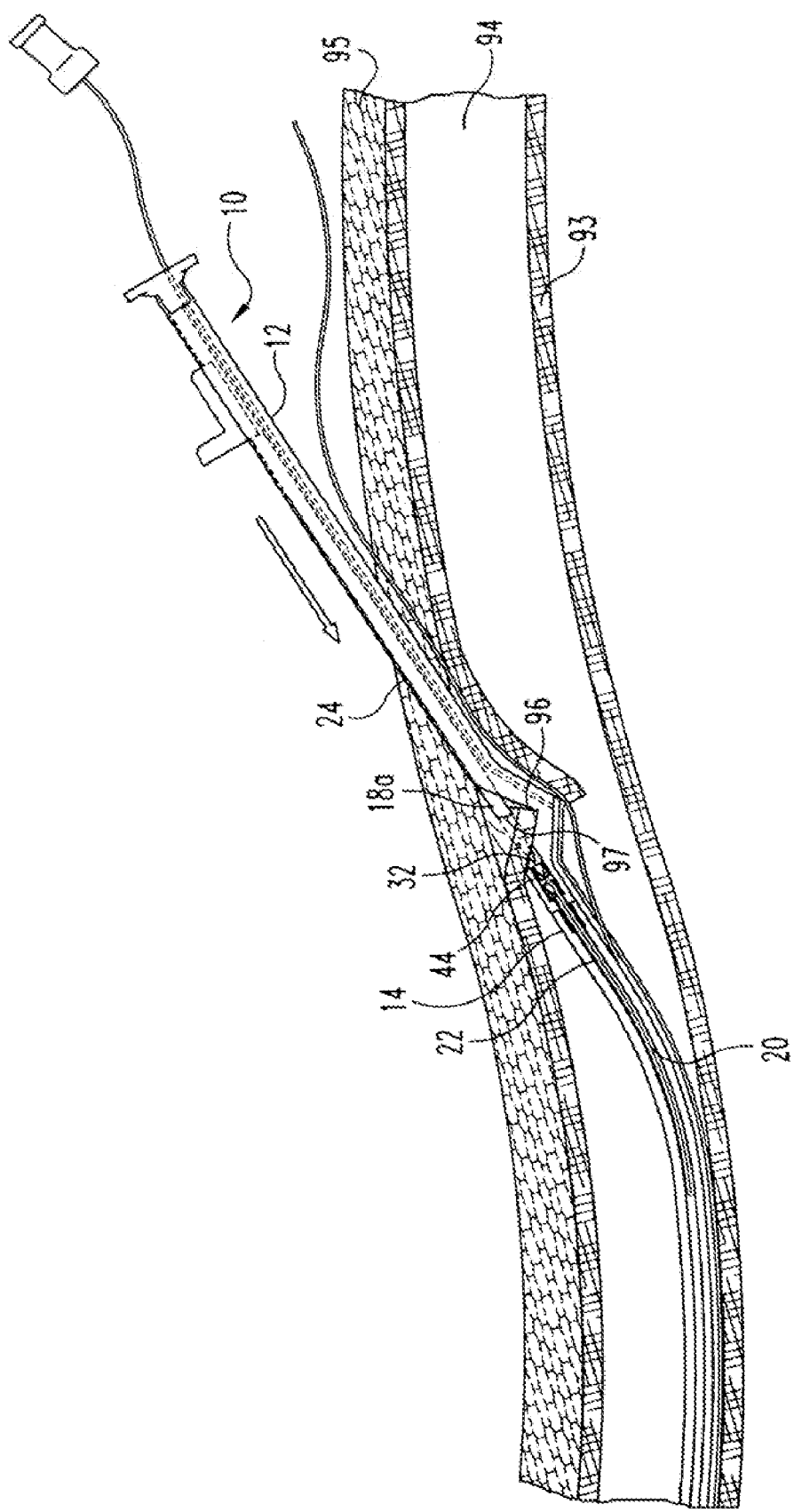
Figure 11:
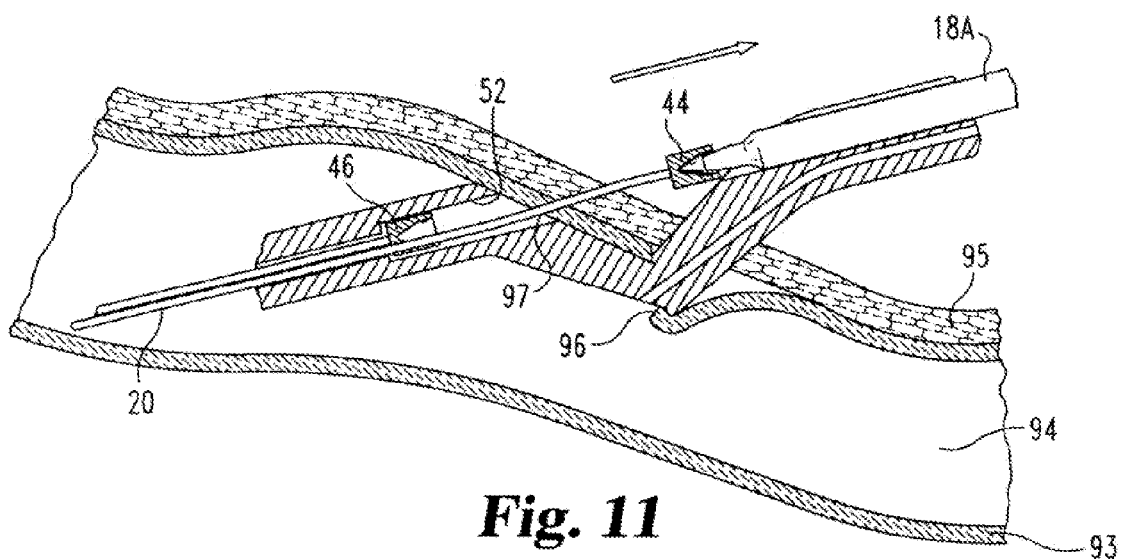

FIG. 10 illustrates suturing device 10 at a first suture position with needle 18a advancing distally through channel 24 and piercing the vascular tissue of vessel 93 at a first suture site 97 on a first side of wound 96. From there, needle tip 32 advances into to receptacle 22 to engage in a first ferrule 44. Once engaged with ferrule 44, first needle 18a can then be withdrawn back through opening 52 in distal member 14 and through first suture site 97, drawing a length of suture material 20 through the vascular tissue in a proximal direction as illustrated in FIG. 11. Preferably the needle path in the proximal direction is the same as in the distal direction—provided that the suturing device has not been moved or dislocated. Needle 18a, including a length of suture material 20 can then be removed from suture device 10. Alternatively, needle 18a and/or a length of suture material can be retained with suture device 10 for subsequent retrieval and use in securing the wound closure.

Figure 12:
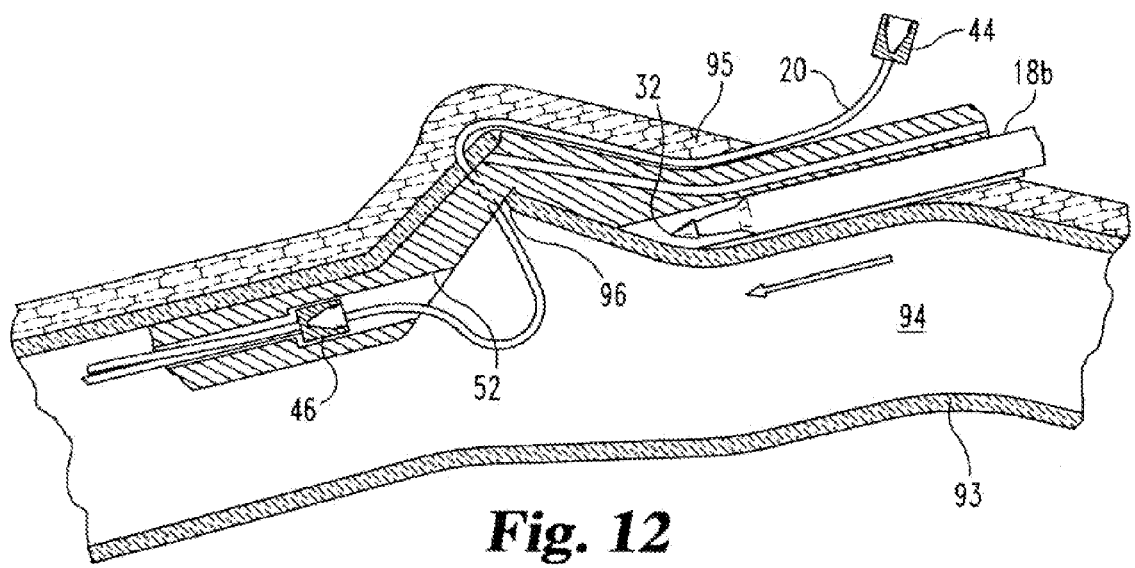
Figure 13:
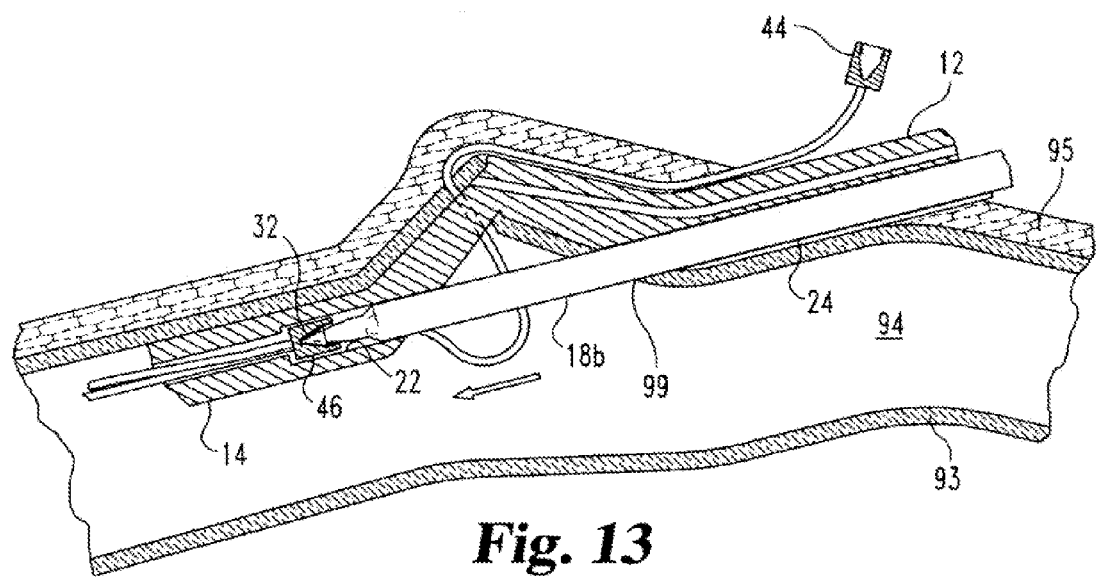
Figure 14:
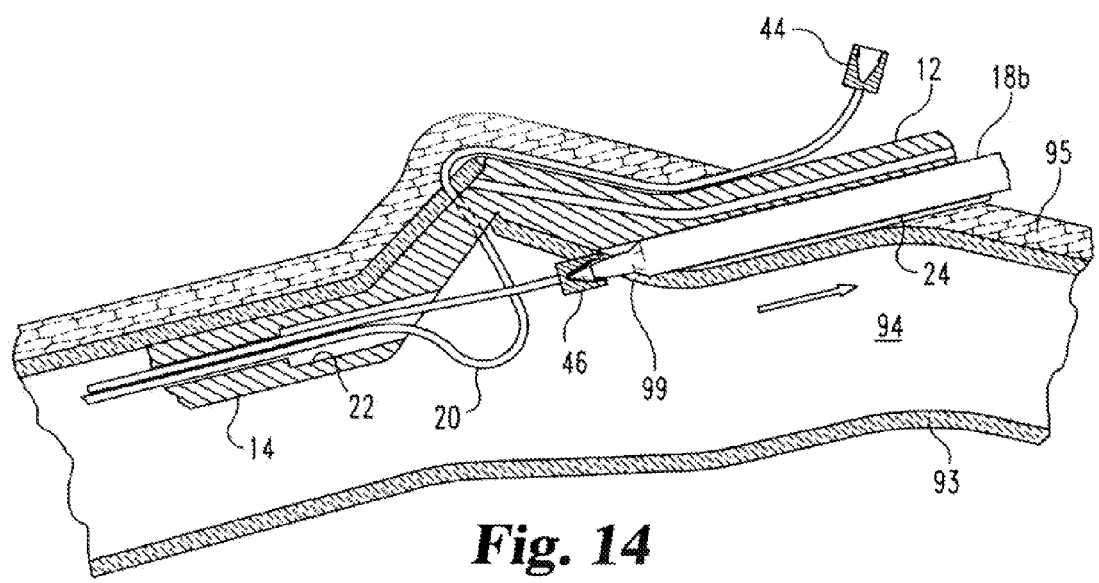
Figure 15:
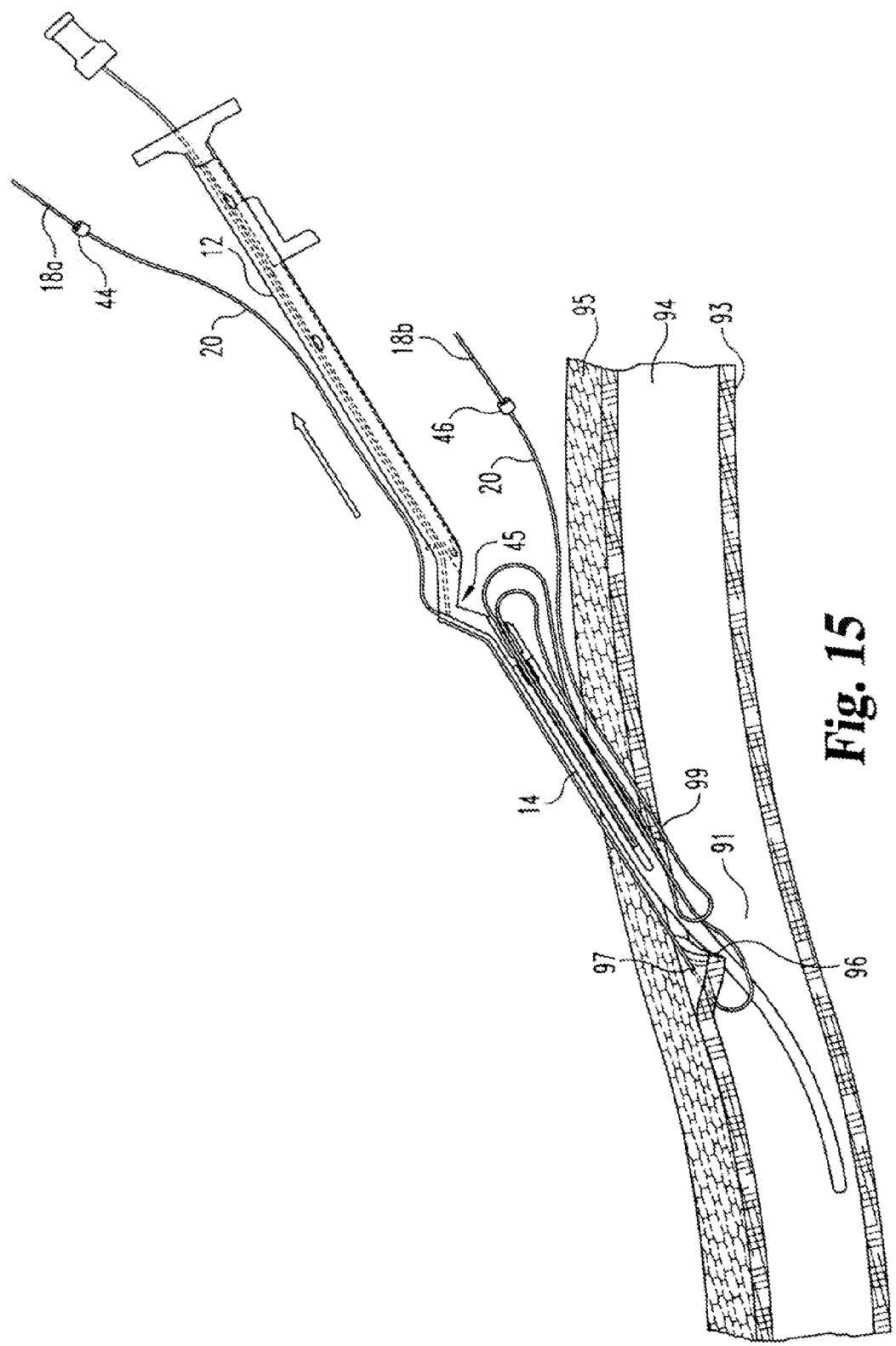

Thereafter, suture device 10 is rotated into a second suture position as illustrated in FIG. 12. For example, suture device 10 may be rotated approximately 180° so that in the second suture position, suture device 10 is positioned to operate on a second side of puncture 96 diametrically opposite first suture site 97. After ensuring that the suturing device is correctly positioned, the procedure described above for needle 18a can be followed. At the second suture position, a second needle 18b is distally advanced using a needle pusher, either the same needle pusher or a second, different needle pusher, through channel 24 to engage in and pierce the vascular tissue 93 received within tissue receiving area 45 at second suture site 99. Again, needle 18b is advanced to enter receptacle 22 and there engage with second ferrule 46 as shown in FIG. 13. Withdrawal of the needle pusher concomitantly withdraws ferrule 46, and a length of suture 20 through second suture site 99 as shown in FIG. 14. Needle 18b and the attached ferrule 46 and length of suture material can be retrieved by the surgeon either by hand or received within a slot in the proximal member. Thereafter, if desired, the process can be repeated, rotating suturing device 10 through about 90° and again, advancing a needle to engage in a subsequent ferrule located in receptacle 22. This process can be repeated as desired and as provided with a number of needles and/or suture materials with ferrules in receptacle 22. It will be understood that in one embodiment, first and second lengths of suture materials are two ends of the same suture. In other embodiments, lengths of suture material are separate pieces of suture. Thereafter, device 10 can be withdrawn from the body as illustrated in FIG. 15.

Figure 16:
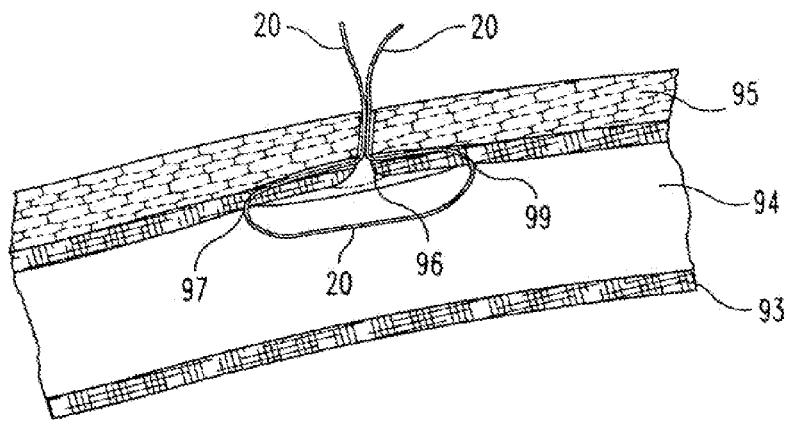

As illustrated in FIG. 16 the lengths of suture material 20 can be gathered. The length of suture material can be separated from the needles. Pulling the lengths of suture material taut closes the wound 96 in the vessel 93. In this embodiment, the path of the suture material passes through vascular tissue on a first side of the wound into the lumen 94 of the vessel 93, across the wound 96—again in the lumen 94—and then out through the vascular tissue 93 on a second or opposite side of the wound. A surgical knot can be tied securing the wound closure. A knot pusher, for example, the knot pushers described in U.S. Pat. No. 5,304,184 issued to Hathaway et al., U.S. Pat. No. 5,746,755 issued to Wood et al., and U.S. Pat. No. 6,132,439 issued to Kontos, can be used to advance the loosely tied knot to the exterior surface of the vascular vessel. In selected embodiments, the surgeon can then tie a suitable surgical knot using the respective lengths of suture material to close the puncture wound 96. In other embodiments, the suture material can be secured using a variety of knot replacement technologies such as that disclosed in U.S. patent application Ser. No. 10/164,606 (US Patent Publication No. 2003/0229377) and in 10/305,923 (US Patent Publication No. 2004/0102809) and depicted in FIGS. 21 and 22. Each of the above-noted references are incorporated by reference in their entirety.

Figure 17:
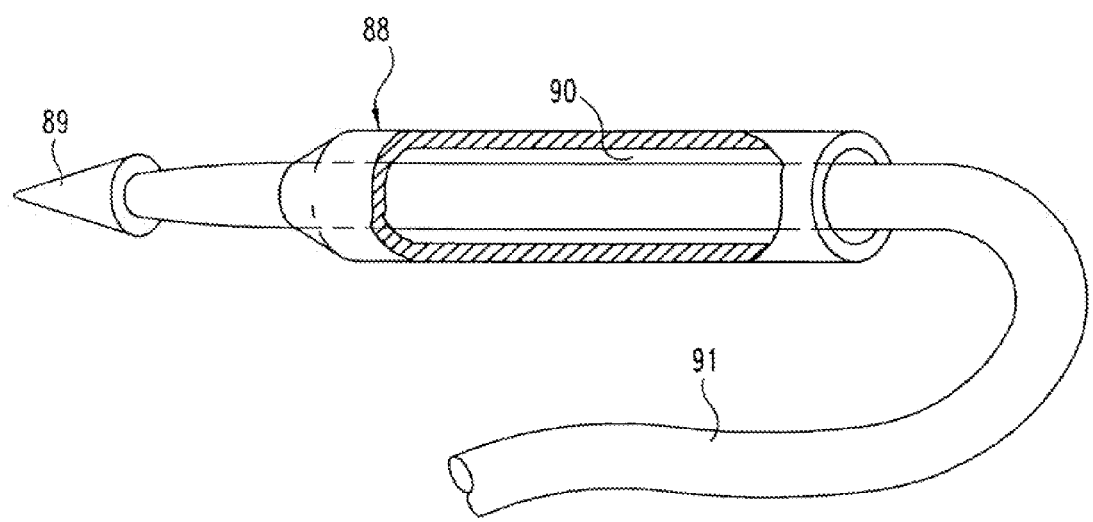
FIG. 17 is a perspective view of a hollow needle for use in the suturing devices described herein.

FIG. 17 is a perspective view of one embodiment of a hollow needle 88 for use in accordance with the present invention. Needle 88 includes a detachable tip 89, a hollow shaft 90, and a length of suture material 91. The length of suture material 91 extends out the proximal end of hollow needle 88. In one embodiment, one end of the suture material 91 is attached to needle tip 89. In this embodiment, the needle tip 89 can be used to pull suture material 91 through a portion of a suturing device or through vascular tissue as discussed more fully below.

Figure 18:
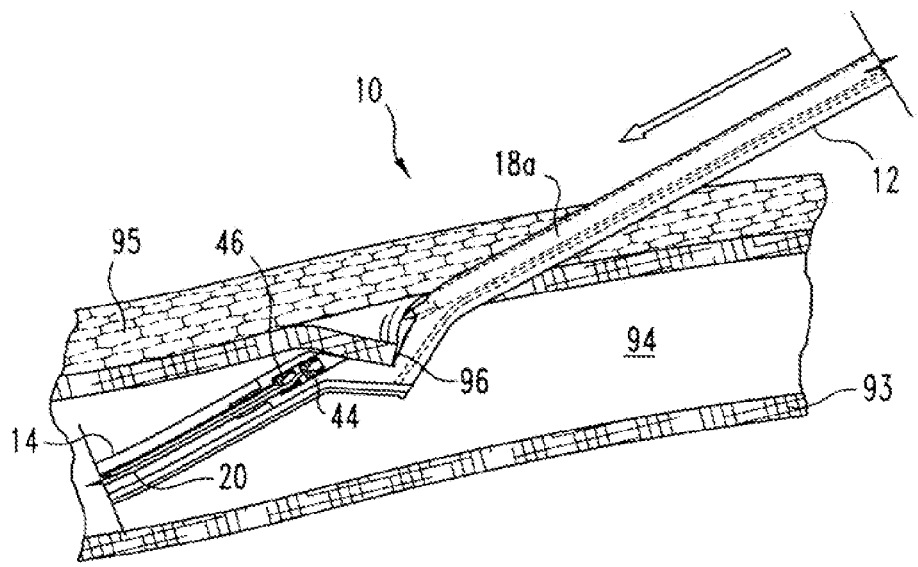
FIGS. 18-20 illustrate the use of the suturing device of FIG. 1 with a hollow needle of FIG. 17.
Figure 19:
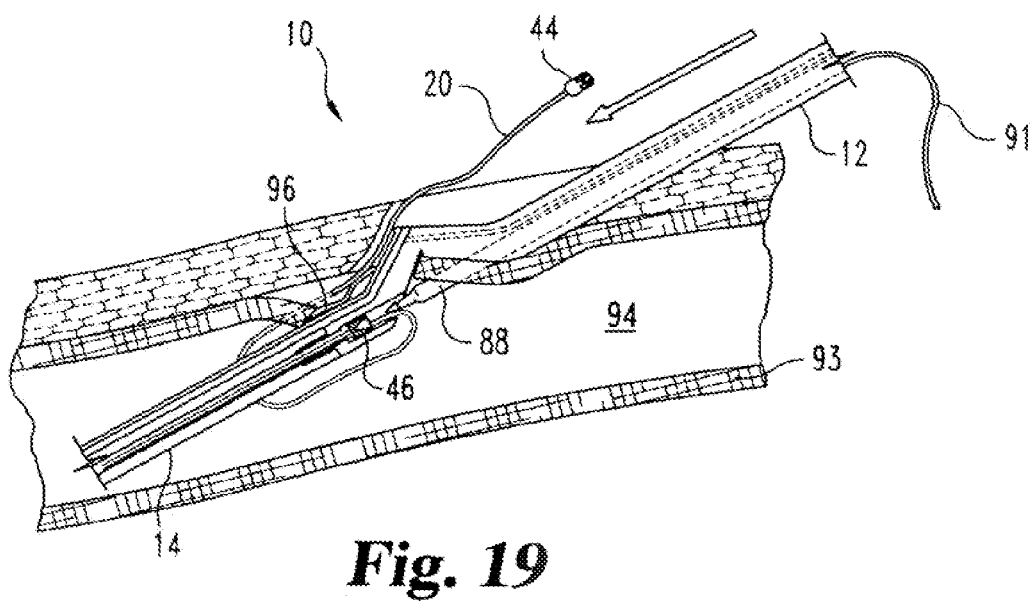
Figure 20:
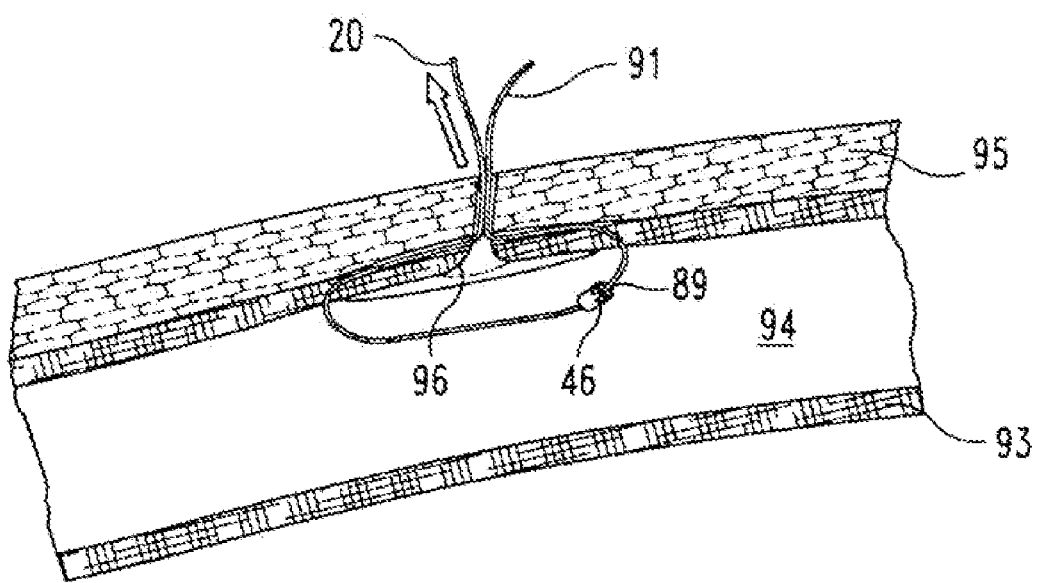

FIGS. 18 through 20 illustrate the use of hollow needles with the suturing device 10. The suturing device 10 is inserted into the vascular vessel as described above and illustrated in FIG. 9. After suturing device 10 has been positioned within the lumen 94 as desired, needle 88 is advanced in the distal direction through needle channel 24 to pierce vascular tissue 93 adjacent the wound 96 in the vessel and then into recess 22 to engage with a first ferrule 44. Needle 88, the attached ferrule 44, and a length of suture material 20 are withdrawn in the proximal direction back through the needle path through a first suture site.

Suturing device 10 can be rotated about its longitudinal axis while maintaining the distal member within the vascular lumen to a second suturing position. FIG. 19 illustrates the advancement of hollow needle 88 along channel 24. Hollow needle 88 can pierce vascular tissue 93 at a second suture site. Needle tip 89 can then engage with the second ferrule 46 located in receptacle 22. Once engaged to second ferrule 46, needle tip 89 can be separated from shaft 90 by withdrawal of the needle shaft 90 back through the second suture site. The needle shaft can be received in or through channel 24. Suture material 91 is then connected to suture material 20 via ferrule 46 and needle tip 89. Suturing device 10 can then be removed from the vascular vessel and eventually from the patient.

Referring now FIG. 20, suture material 20 and 91 are connected together using second ferrule 46 and needle tip 89.

The connected suture material can be pulled in either direction by 1) pulling on suture material 20 in the distal direction to draw ferrule 46, needle tip 89, and a portion of suture material 91 through the second suture site, or 2) pulling on suture material 91 in the distal direction to draw ferrule 46, needle tip 89, and a portion of suture material 20 through the second suture site. In yet other embodiments, the free ends of suture material 20 and 91 can be pulled taut to close the vascular wound. Preferably in this embodiment both of needle tip 89 and ferrule 46 (as well as the suture materials) are composed of a biodegradable material to biodegrade. Biodegradable materials for the ferrule, needle tips, and suture material are well known in the art and these materials are useful to prepare the components of the present invention.

Figure 21:
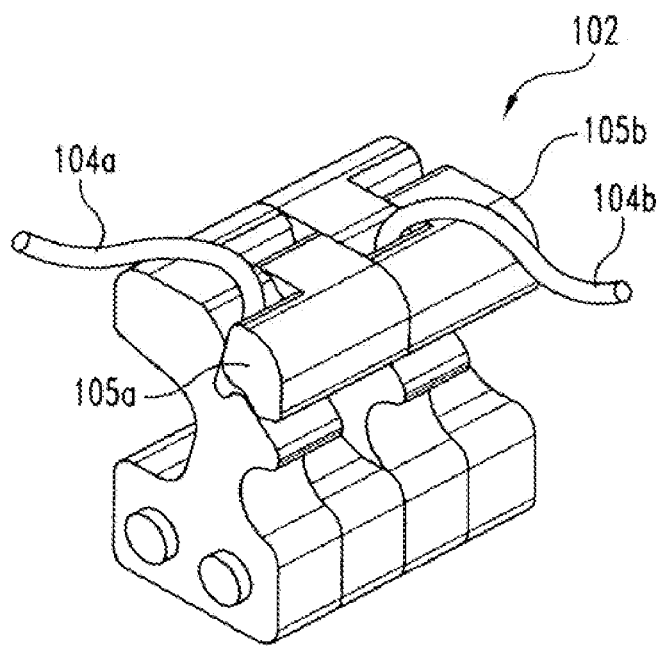
FIG. 21 is a perspective view of one embodiment of a suture securing device for use in the present invention.

FIG. 21 is a perspective view of a suture securing device 102 for use in the present invention. Suture clamping device 102 is described and illustrated in US Patent Publication No. 2004/0102809 which is incorporated herein by reference. In use, device 102 can secure ends of one, two, three or more lengths of suture material. Two lengths of suture material 104a and 104b are illustrated with device 102. The lengths of suture material are threaded into the flexible elements 105a and 105b which are then locked or fixed together clamping the suture material therein.

Figure 22:
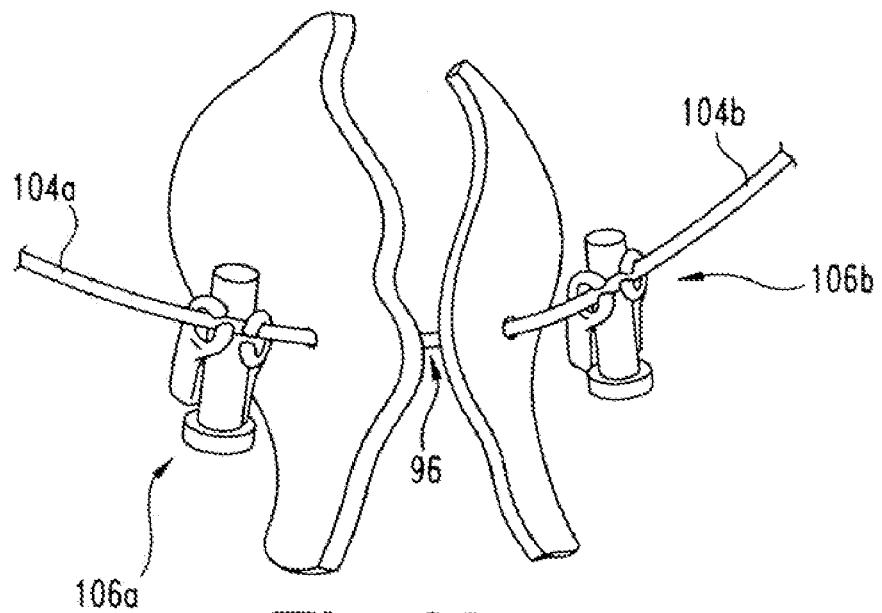
FIG. 22 is a perspective view of an alternative embodiment of a suture securing device for use in the present invention.

FIG. 22 shows another embodiment of suture clamping devices 106a and 106b for use in the present invention. Devices 106a and 106b are described in US Patent Publication No. 2003/0229377 which is incorporated herein by reference in its entirety. Devices 106a and 106b cooperate by separately clipping onto a selected length of suture material 104a or 104b which have previously pulled taut to close the wound 96 or complete the surgical procedure.

The devices prevent the suture material from regressing back through the sutured tissue.

The present invention provides a variety of means, devices and methods for closing wounds in tissue and is particularly, but not exclusively, suitable for vascular tissue. It will be understood that the present invention contemplates modifications as would occur to those skilled in the art without departing from the spirit of the present invention. In addition, where the various structures, elements, and procedural steps or stages have been described with reference to a specified embodiment and device. Each of the individual or a combination of the structures, elements, and procedural steps or stages are contemplated to be combinable with each of the other embodiments and devices described herein and as such are contemplated to be within the scope of the present invention.

Further, all publications, patents, and patent applications cited in this specification are herein incorporated by reference as if each individual publication, patent, or patent application was specifically and individually indicated to be incorporated by reference and set forth in its entirety herein. Further, any theory of operation, proof, or finding stated herein is meant to further enhance understanding of the present invention and is not intended to make the scope of the present invention dependent upon such theory, proof, or finding.

What is claimed is:

1. A method of suturing an opening in a vascular vessel, said method comprising:
   inserting a vascular suturing device through the opening in the vascular vessel, said suturing device comprising:
   a proximal member having a single needle channel configured to receive a plurality of needles;
   a distal member configured to be inserted into the lumen of the vascular vessel, the distal member having a single cavity therein and a length of suture material disposed in the single cavity; and a connecting member between the proximal and distal members;

distally advancing a first needle of the plurality of needles through the single needle channel, sufficient to pierce a portion of tissue adjacent the opening in the vessel extend into the single cavity of the distal member;

capturing the suture within the single cavity with the first needle, the first needle engaging a first needle engaging fitting connected to the length of suture;

retracting the first needle carrying a first portion of the suture back through the tissue and the single needle channel; and distally advancing a second needle of the plurality of needles through the single needle channel following retraction of the first needle through the single needle channel to capture a second portion of the suture connected to a second needle engaging fitting, the first needle engaging fitting has a cross-sectional diameter greater than that of the second needle engaging fitting.

2. The method of claim 1 comprising repositioning the suturing device within the lumen and advancing the second needle of the plurality of needles through the single needle channel to the suture within the cavity.

3. The method of claim 2 wherein the suture comprises two needle engaging fittings.

4. The method of claim 3 comprising retracting the second needle of the plurality of needles carrying the second portion of the suture back through the tissue and the single needle channel to leave a loop of suture within the cavity.

5. The method of claim 4 comprising securing the first and second portions of the suture together to promote hemostasis.

6. The method of claim 5 wherein said securing comprises tying the first and second portions of suture together.

7. The method of claim 5 wherein said securing comprises clamping the first and second portions of suture together with a suture clamp.

8. A method of suturing an opening in a vascular vessel, said method comprising:

inserting a vascular suturing device through the opening in the vascular vessel, said suturing device comprising:

a proximal member including an elongate body having a single needle channel therethrough sized to receive at one time a single needle of a plurality of needles therein;

a distal member configured to be inserted into the lumen of the vascular vessel, said member having a receptacle located therein, and a length of suture material being stored in the distal member; and an intermediate member disposed between the proximal member and the distal member, said intermediate member defining a tissue receiving area and having a first opening providing a passageway to the channel and a second opening providing a passageway into the receptacle;

distally advancing a first needle of the plurality of needles through the needle channel, which is configured to receive only the single needle of the plurality of needles at one time, sufficient to pierce a first portion of tissue adjacent the opening in the vessel and to extend into the cavity of the distal member;

capturing a first portion of the suture within the cavity with the first needle, the first needle engaging a first needle engaging fitting connected to the length of suture;

retracting the first needle carrying the first portion of the suture back through the tissue and the channel; and distally advancing a second needle of the plurality of needles through the same single needle channel following retraction of the first needle through the single needle channel to capture a second portion of the suture connected to a second needle engaging fitting, the first needle engaging fitting has a cross-sectional diameter greater than that of the second needle engaging fitting.

9. The method of claim 8, wherein the second needle is advanced through the needle channel from a needle cartridge slidably mounted on the proximal member and containing a plurality of needles.

10. The method of claim 9, further comprising retracting the second needle carrying the second portion of the suture back through the tissue and the channel.

11. The method of claim 10, wherein the first needle engaging fitting is disposed proximal to the second needle engaging fitting within the receptacle.

12. A method of suturing an opening in a vascular vessel, said method comprising:

inserting a vascular suturing device through the opening in the vascular vessel, said suturing device comprising:

a proximal member including an elongate body having a needle channel therethrough sized to receive a single needle therein;

a distal member configured to be inserted into the lumen of the vascular vessel, said member having a receptacle located therein, and a length of suture material being stored in the distal member;

an intermediate member disposed between the proximal member and the distal member, said intermediate member defining a tissue receiving area and having a first opening providing a passageway to the channel and a second opening providing a passageway into the receptacle;

advancing a first needle through the needle channel, sufficient to pierce a first portion of tissue adjacent the opening in the vessel and to extend into the cavity of the distal member;

capturing the suture within the cavity with the first needle;

wherein capturing the suture within the cavity with the first needle, comprises the first needle engaging a first needle engaging fitting connected to the length of suture;

retracting the first needle carrying a first portion of the suture back through the tissue and the channel;

advancing a second needle through the needle channel, sufficient to pierce a second portion of tissue adjacent the opening in the vessel and to extend into the cavity of the distal member;

wherein the second needle is advanced through the needle channel from a needle cartridge slidably mounted on the proximal member and containing a plurality of needles, capturing the suture within the cavity with the second needle;

wherein capturing the suture within the cavity with the second needle, comprises the second needle engaging a second needle engaging fitting connected to the length of suture;

wherein the first needle engaging fitting is disposed proximal to the second needle engaging fitting within the receptacle and the first needle engaging fitting has a cross-sectional diameter greater than that of the second needle engaging fitting; and retracting the second needle carrying a second portion of the suture back through the tissue and the channel.

13. The method of claim 12 comprising securing the first and second portions of the suture together to promote hemostasis.

14. The method of claim 12 wherein said securing comprises tying the first and second portions of suture together.

15. The method of claim 12 wherein said securing comprises clamping the first and second portions of suture together with a suture clamp.

* * * * *